United States Patent [19]

Zydowsky

[11] Patent Number: 5,268,476
[45] Date of Patent: Dec. 7, 1993

[54] SUBSTITUTED 10BH-OXAZOLO[3,2-C] [1,3] BENZOXAZINE-2(3H), 5-DIONES

[75] Inventor: Thomas M. Zydowsky, Waukegan, Ill.

[73] Assignee: Abbott Laboratories, Abbott Park, Ill.

[21] Appl. No.: 909,524

[22] Filed: Jul. 6, 1992

Related U.S. Application Data

[60] Division of Ser. No. 647,877, Jan. 30, 1991, Pat. No. 5,153,358 which is a continuation-in-part of PCT/US89/4649, Oct. 18, 1989, which is a continuation-in-part of Ser. No. 390,571, Aug. 7, 1989, abandoned, which is a continuation-in-part of Ser. No. 259,959, Oct. 19, 1988, abandoned.

[51] Int. Cl.$^5$ .................................. C07D 263/08
[52] U.S. Cl. ............................................... 544/89
[58] Field of Search ...................................... 544/89

[56] References Cited

U.S. PATENT DOCUMENTS

| | | | |
|---|---|---|---|
| 4,264,771 | 4/1981 | Steglich et al. | 562/443 |
| 4,371,706 | 2/1983 | Edmonds et al. | 562/553 |
| 4,508,921 | 4/1985 | Amato et al. | 562/443 |
| 5,164,388 | 11/1992 | De | 514/238 |

FOREIGN PATENT DOCUMENTS

WO90/04917  5/1990  PCT Int'l Appl.

OTHER PUBLICATIONS

Zydowsky et al. Jour. Org. Chem. vol. 55 pp. 5437–5439 (1990).
Zydowsky, et al., Abstract No. ORGN 240, 199th Amer. Chem. Soc. Nat. Mtg. Apr. 22–27, 1990.
Block, et al. J. Chem. Soc. (C) 329 (1971).
Schollkopf, Angew, Chem. Int. Ed. Engl. 2 117 (1978).
Schollkopf, Synthesis 271 (1984).
Schollkopf, Liebigs Ann. Chem. 399 (1987).
Seebach, Helv. Chim. Acta 68 1243 (1985).
Belokon, J. Chem. Soc., Chem. Commun 171 (1985).
Ihara, J. Org. Chem. 54 5413 (1989).
Ojima, Tetrahedron 5307 (1988).
Fitzi, Tetrahedron 44 5277 (1988).
Kruizinga, J. Org. Chem. 53 1826 (1988).
Fadel, Tet. Lett. 28 2243 (1987).

*Primary Examiner*—Donald G. Daus
*Attorney, Agent, or Firm*—Steven R. Crowley

[57] ABSTRACT

A novel process for the preparation of α-alkylated α-amino acids and α-halogenated α-amino acids is disclosed. These α-alkylated α-amino acids and α-halogenated α-amino acids are useful as intermediates for the preparation of enzyme inhibitors (for example, renin inhibitors) and other peptides or amino acid derivatives or analogs.

5 Claims, No Drawings

SUBSTITUTED 10BH-OXAZOLO[3,2-C] [1,3] BENZOXAZINE-2(3H), 5-DIONES

This is a division of U.S. patent application Ser. No. 647,877, filed Jan. 30, 1991, now U.S. Pat. No. 5,153,358, which is a continuation-in-part of U.S. patent application Ser. No. PCT/US89/04649, filed Oct. 18, 1989, which is a continuation-in-part of U.S. patent application Ser. No. 390,571, filed Aug. 7, 1989, which is a continuation-in-part of U.S. patent application Ser. No. 259,959, filed Oct. 19, 1988 (now both abandoned).

TECHNICAL FIELD

The present invention relates to a novel process for the preparation of α-alkylated α-amino acids and α-halogenated α-amino acids. These α-alkylated α-amino acids and α-halogenated α-amino acids are useful as intermediates for the preparation of enzyme inhibitors (for example, renin inhibitors) and other peptides or amino acid derivatives or analogs.

BACKGROUND ART

A variety of methods have been developed for the synthesis of α-alkylated α-amino acids. Many of these methods involve the use of chiral auxiliaries or multiple step reaction sequences (Schollkopf, Angew. Chem. Int. Ed. Engl. 2 117 (1978); Schollkopf, Syntheis 271 (1984); Schollkopf, Liebigs Ann. Chem. 399 (1987); Seebach, Helv. Chim. Acta 68 1243 (1985); Belokon, J. Chem. Soc., Chem. Commun. 171 (1985); Ihara, J. Org. Chem. 54 5413 (1989); Ojima, Tetrahedron 5307 (1988); Fitzi, Tetrahedron 44 5277 (1988); Fadel, Tet. Lett. 28 2243 (1987)). One method involves the enzymatic resolution of a racemic α-alkylated α-amino acid (Kruizinga, J. Org. Chem. 53 1826 (1988). Some of the methods cited involve reaction conditions which are not compatible with functional groups that would be desirable to introduce in the side chain of an α-alkylated α-amino acid. Furthermore, some of the methods cited do not produce α-alkylated α-amino acids in high optical purity.

As a result, there is a continuing need for methods that are simple, use inexpensive reagents and produce α-alkylated α-amino acid products in good yield and high optical purity.

DISCLOSURE OF THE INVENTION

The present invention relates to a process for the preparation of α-alkylated α-amino acids and α-halogenated α-amino acids comprising alkylation or halogenation of an oxazolidinone of the formula I wherein s is 0 to 4; R is (i) loweralkyl, (ii) cycloalkyl, (iii) loweralkenyl, (iv) loweralkynyl, (v) aryl, (vi) arylalkyl, (vii) heterocyclic, (viii) (heterocyclic)alkyl, (ix) —COOH, (x) alkoxycarbonyl, (xi) —$(CH_2)_m$—Q—$R^3$ wherein m is 0 to 4, Q is O or S and $R^3$ is hydrogen, loweralkyl, an O-protecting group or an S-protecting group, or (xii) —$(CH_2)_p$—N($R^4$)($R^5$) wherein p is 0 to 4 and $R^4$ and $R^5$ are independently selected from hydrogen, loweralkyl, benzyl and an N-protecting group; and $R^6$ and $R^7$ are independently selected from hydrogen, loweralkyl, halogen, nitro, alkoxy, haloalkyl and alkoxycarbonyl with (1) an alkylating agent of the formula $R^1$—X wherein $R^1$ is loweralkyl, —$(CH_2)_u$CN wherein u is 1 to 3, cycloalkylalkyl, loweralkenyl, loweralkynyl, arylalkyl, (heterocyclic)alkyl or —$(CH_2)_z$CH(OR'')(OR''') wherein z is 1 to 3 and R'' and R''' are loweralkyl or aryl or R'' and R''' taken together are —(CH($R^0$))$_t$— wherein t is 2 to 3 and $R^0$ is independently selected at each occurrence from hydrogen, loweralkyl and aryl, and X is a leaving group or (2) a halogenating agent such as N-bromosuccinimide, N-chlorosuccinimide, N-iodosuccinimide, N-fluoro-3,3-dimethyl-2,3-dihydro-1,2-benthizol-1,1-dioxide, N-fluoro-2-pyridone, N-fluoroquinuclidinium fluoride and the like to provide compounds III or IV wherein $R^1$ is halogen. Leaving groups (X) include halogen, sulfonates (such as mesylate, tosylate, triflate and the like) and quaternary ammonium groups and the like Oxazolidinone I is treated with 0.95 to 1.00 equivalents (preferably, 0.98 equivalents) of a strong base such as lithium bis(trimethylsilyl)amide, sodium bis(trimethylsilyl)amide, lithium diisopropylamide or lithium tetramethylpiperidine and the like (preferably, lithium bis(trimethylsilyl)amide or sodium bis(trimethylsilyl)amide) in a solvent such as tetrahydrofuran (THF), diethyl ether or 1,2-dimethoxyethane (DME) and the like (preferably, THF) at a temperature of −56° C. to −78° C. 1.0 to 4.0 equivalents (preferably 2.0 equivalents) of an additive such as 1,3-dimethyl-3,4,5,6-tetrahydro-2(1H)-pyrimidinone (DMPU), hexamethylphosphoramide (HMPA) or lithium bromide and the like (preferably, DMPU or HMPA) is added, followed by the alkylating agent (1.0 to 4.0 equivalents, preferably, 2.0 equivalents) or the halogenating agent (1.0 to 4.0 equivalents, preferably, 2.0 equivalents). After stirring for 30 minutes to 24 hours (preferably, 1 to 4 hours), the solution is acidified (preferably with saturated aqueous citric acid) and the alkylated or halogenated ($R^1$ is halogen) oxazolidinone II is isolated.

Oxazolidinone II can be treated with 10 to 40 equivalents (preferably 30 to 40 equivalents) of a hydroxide such as lithium hydroxide, sodium hydroxide, potassium hydroxide and the like (preferably lithium hydroxide) in a solvent such as aqueous dioxane, aqueous THF or aqueous DMF and the like (preferably 35% aqueous dioxane) to provide the α-alkylated (or halogenated) α-amino acid III. Alternatively, oxazolidinone II can be hydrolyzed under acidic conditions by treatment with 20 to 50 equivalents (preferably 30 to 40 equivalents) of an acid such as hydrochloric acid, hydrobromic acid, methanesulfonic acid, trifluoroacetic acid and the like (preferably hydrochloric acid) in a solvent such as aqueous dioxane, aqueous THF, aqueous methanol, aqueous ethanol, and the like (preferably aqueous dioxane or aqueous methanol) to provide the α-alkylated (or halogenated) α-amino acid III. Alternatively, oxazolidinone II can be hydrolyzed under acidic conditions by treatment with 5 to 25 equivalents by weight (preferably 10 to 20 equivalents) of $FeCl_3/SiO_2$ in acids such as hydrochloric acid, hydrobromic acid and the like (preferably hydrochloric acid) to provide the α-alkylated (or halogenated) α-amino acids.

Oxazolidinone II can also be treated with 10 to 40 equivalents (preferably 30 to 40 equivalents) of an alkoxide such as a loweralkoxide (MOR² wherein M is lithium, sodium or potassium and R² is loweralkyl, for example, sodium methoxide in methanol, potassium methoxide in methanol or sodium ethoxide in ethanol) or benzyloxide (MOR² wherein M is lithium, sodium or potassium and R² is benzyl, for example, sodium benzyloxide in benzyl alcohol) and the like to provide the protected α-alkylated (or halogenated) α-amino ester IV.

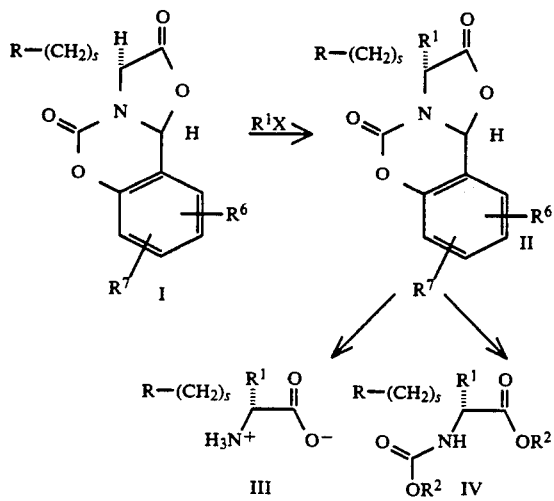

Oxazolidinone I can be prepared by reacting salicylaldehyde (or substituted salicylaldehyde), triphosgene (or phosgene) and the appropriate α-amino acid under anhydrous conditions. The schemes provided herein illustrate the process of the invention wherein the L-amino acid is one of the starting materials. However, products III and/or IV having the opposite stereochemistry can be obtained by starting with the corresponding D-amino acid.

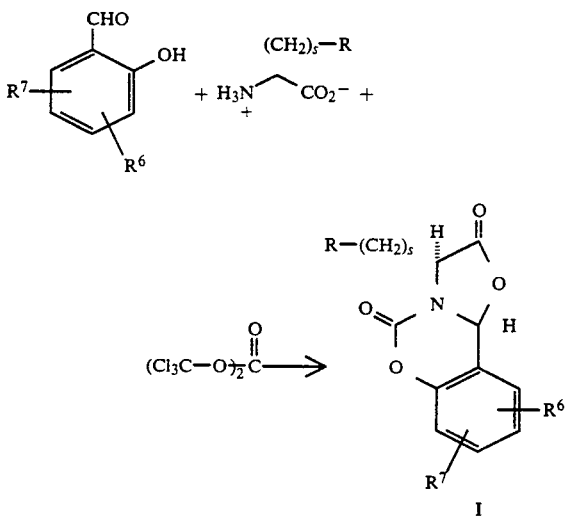

Alkylated α-amino acids such as III and IV can be used as intermediates for the preparation of renin inhibitors. (See PCT Patent Application No. WO90/04917, published May 17, 1990).

The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, tert-butyl, n-pentyl, 1-methylbutyl, 2,2-dimethylbutyl, 2-methylpentyl, 2,2-dimethylpentyl, n-hexyl and the like.

The term "loweralkenyl" as used herein refers to a loweralkyl radical of 2 to 7 carbon atoms which contains at least one carbon-carbon double bond. Loweralkenyl groups can be unsubstituted or substituted with one, two or three substituents independently selected from loweralkyl, loweralkenyl, loweralkynyl, aryl, arylalkyl, cycloalkyl, heterocyclic and alkoxycarbonyl.

The term "loweralkynyl" as used herein refers to a loweralkyl radical of 3 to 7 carbon atoms which contains at least one carbon-carbon triple bond. Loweralkynyl groups can be unsubstituted or substituted with a substituent selected from loweralkyl, loweralkenyl, loweralkynyl, aryl, arylalkyl, cycloalkyl, heterocyclic and alkoxycarbonyl.

The term "cycloalkyl" as used herein refers to an aliphatic ring having 3 to 7 carbon atoms.

The term "cycloalkylalkyl" as used herein refers to a loweralkyl radical to which is appended a cycloalkyl group including, but not limited to, cyclopropylmethyl, cyclopentylmethyl, cyclohexylmethyl and the like.

The term "aryl" as used herein refers to a monocyclic or bicyclic carbocyclic ring system having one or more aromatic rings including, but not limited to, phenyl, naphthyl, tetrahydronaphthyl, indanyl, biphenyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "arylalkyl" as used herein refers to an aryl group appended to a loweralkyl radical including, but not limited to, benzyl, phenethyl, naphthylmethyl, 4-methoxybenzyl and the like.

The term "heterocyclic" as used herein refers to any 3- or 4-membered ring containing a heteroatom selected from oxygen, nitrogen and sulfur; or a 5- ro 6-membered ring containing one, two or three nitrogen atoms; one nitrogen and one sulfur atom; or one nitrogen and oxygen atom. The 5-membered ring has 0–2 double bonds and 6-membered ring has 0–3 double bonds. The nitrogen and sulfur heteroatoms can be optionally oxidized. The nitrogen heteroatoms can be optionally quaternized. The term "heterocyclic" also includes bicyclic groups in which any of the above-mentioned heterocyclic rings is fused to a benzene ring or a cyclohexane ring or another heterocyclic ring.

Heterocyclics can be unsubstituted or substituted with one or two substituents independently selected from hydroxy, halo, oxo (=O), alkylimino (R*N= wherein R* is a loweralkyl group), amino, alkylamino, dialkylamino, alkoxy, polyalkoxy, haloalkyl, cycloalkyl, aryl, arylalkyl, carboxy, —SO₃H and loweralkyl.

Heterocyclics include: pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

The term "(heterocyclic)alkyl" as used herein refers to a heterocyclic group appended to a loweralkyl radical.

The terms "alkoxy" and "thioalkoxy" as used herein refer to $R^{10}O—$ and $R^{10}S—$, respectively, wherein $R^{10}$ is a loweralkyl group.

The term "alkoxycarbonyl" as used herein refers to $R^{20}OC(O)—$ wherein $R^{20}$ is a loweralkyl group.

The term "halo" or "halogen" as used herein refers to I, Br, Cl or F.

The term "haloalkyl" as used herein refers to a loweralkyl radical in which one or more hydrogen atoms is replaced by a halogen including, but not limited to, fluoromethyl, 2-chloroethyl, trifuoromethyl, 2,2-dichloroethyl and the like.

The term "alkylamino" as used herein refers to —NHR[11] wherein R[11] is a loweralkyl group.

The term "dialkylamino" as used herein refers to —NR[12]R[13] wherein R[12] and R[13] are independently selected from loweralkyl.

The term "alkoxycarbonyl" as used herein refers to —C(O)OR[14] wherein R[14] is a loweralkyl group.

The term "polyalkoxy" as used herein refers to —OR[15] wherein R[15] is a straight or branched chain containing 1-5 $C_n$—O—$C_{n'}$ linkages wherein n and n' are independently selected from 1 to 3 including, but not limited to, methoxyethoxymethoxy, ethoxyethoxymethoxy and the like.

The term "N-protecting group" as used herein refers to those groups intended to protect a nitrogen atom or amino group against undesirable reactions during synthetic procedures and includes those N-protecting groups disclosed in Greene, "Protective Groups In Organic Synthesis" (John Wiley & Sons, New York (1981)) such as acetyl, benzoyl, benzyl, phthaloyl, t-butoxycarbonyl (Boc), benzyloxycarbonyl (Cbz) and the like.

The term "O-protecting group" as used herein refers to those groups intended to protect a hydroxy group against undesirable reactions during synthetic procedures and includes those O-protecting groups disclosed in Greene, "Protective Groups In Organic Synthesis" (John Wiley & Sons, New York (1981)) such as acetyl, benzoyl, t-butyl, benzyl and the like.

The term "S-protecting group" as used herein refers to those groups intended to protect a thiol (—SH) group against undesirable reactions during synthetic procedures and includes those S-protecting groups disclosed in Greene, "Protective Groups In Organic Synthesis" (John Wiley & Sons, New York (1981)) such as acetyl, benzoyl, t-butyl, benzyl and the like.

The following examples will serve to further illustrate the process of the invention.

EXAMPLE 1

(S)-2 Amino-2-phenylmethyl-4 pentenoic acid a.
(3S,11R)-3-Phenylmethyl-10bH-oxazolo[3,2,c][1,3]benzoxazine-2(3H),5-dione Following the procedure of Block (J. Chem. Soc. (C), 329, (1971)), L-Phenylalanine (16.5 g, 100 mmol) was added to a solution of NaOEt (100 mmol) in absolute ethanol (1 L). Salicylaldehyde (12.2 g, 100 mmol) was added and the yellow-green solution was concentrated in vacuo and dried under hi-vac for three h at 50° C. The residue was dissolved in 400 ml of EtOH-free $CHCl_3$ and $K_2CO_3$ (138 g, 1 mol) was added. Mechanical stirring was started and a solution of triphosgene (11 g, 37 mmol) in 100 ml $CHCl_3$ was added dropwise such that the reaction temperature remained at or below 30° C. Stirring was continued for 2-3 h at which time the reaction was filtered and the salts were washed with several portions of solvent. The organic solution was washed with $H_2O$, dried ($MgSO_4$), and concentrated in vacuo. Recrystallization from ethyl acetate-hexane mixtures provided the title compound as a colorless solid (14.2 g, 48%). mp=158°-159° C.; $[\alpha]_D= +150.25°$ (c=1, $CH_2Cl_2$); MS(DCI): 296(M+H)+.

$C_{17}H_{13}NO_4$: Calculated C 69.15; H 4.44; N 4.74 : Found C 69.09; H 4.48; N 4.68.

NMR ($CDCl_3$): 3.37 (dd,1H, $J_1$=9 Hz, $J_2$=4.5 Hz), 3.48 (dd,1H, $J_1$=9 Hz, $J_2$=6 Hz), 4.86 (d,½H, J=6 Hz,), 4.90 (d,½H,J=4.5 Hz), 5.29 (s,1H), 7.10-7.48 (m,9H).

b.
(3S,11R)-3-Phenylmethyl-3-(1-(2-propenyl)-10bH-oxazolo [3,2-c][1,3]benzoxazine-2(3H), 5-dione A solution of the resultant compound from Example 1a (886 mg, 3 mmol) in dry THF (15 ml) was cooled to −78° C. and then treated with a THF solution of lithium bis(trimethylsilyl)amide (1N, 2.94 ml, 2.94 mmol). After the addition of DMPU (1.15 g, 9 mmol), the solution was stirred for 15 min at −78° C. and then treated with allyl bromide (725 mg, 6 mmol). The reaction was stirred for 2 h at −78° C. and then warmed to −20° C. over 2 hr. The reaction was recooled to −78° C. and then acetic acid (100 μl) was added. The solution was concentrated in vacuo and the residue was partitioned between ethyl acetate (200 ml) and saturated aqueous citric acid (100 ml). The layers were separated and the organic layer was washed with additional saturated aqueous citric acid (2×), water (1×), saturated brine (1×), dried ($Na_2SO_4$) and concentrated in vacuo to afford a yellow oil. The oil was dissolved in methylene chloride and passed through a 6" plug of silica gel eluting with 12.5% ethyl acetate/hexane. The eluent (200 ml) was concentrated in vacuo to afford the title compound as a colorless oil (940 mg, 82%) which solidified on standing.

MS(DCI): 336(M+H)+, 353(M+NH_4)+.

c. (S)-2-Amino-2-phenylmethyl-4-pentenoic acid

The resultant compound from example 1b (336 mg, 1 mmol) in 10 ml of dioxane was added to a solution of LiOH(1.68 g,40 mmol) in 35% aqueous dioxane (120 ml). After 20 min the yellow-green solution was acidified to pH=1 with 6N HCl and stirred for 1 h at room temperature. The solution was concentrated and the residue was partitioned between $H_2O$ (25 ml) and $CH_2Cl_2$ (25 ml) . The aqueous layer was washed with $Et_2O$ (1×25 ml) and then concentrated to afford the amino acid salt. The salt was dissolved in 10 ml of $H_2O$ and applied to 100 g of XAD-16 resin. The column was eluted with $H_2O$ until the eluent was free from Cl− and then with 50% aqueous methanol. Ninhydrin positive fractions were pooled and concentrated. Final traces of $H_2O$ were removed with several methanol chases and the title compound was obtained as a colorless solid (384 mg, 94%). $[\alpha]_D= +27.30°$ (c=1,$H_2O$); MS(FAB): 206(M+H)+; NMR($D_2O$): 2.53(dd,1H, $J_1$=15 Hz, $J_2$=8 Hz), 2.81(dd,1H, $J_1$=15 Hz, $J_2$=6 Hz), 3.04(d,1H,J=15 Hz), 3.35(d,1H,J=15 Hz), 5.28(d,1H,J=5 Hz), 5.33(s,1H), 5.77(m,1H), 7.27-7.47(m,5H). $^{13}C$ NMR($D_2O$): 41.24, 42.14, 65.81, 122.27, 128.51, 129.61, 130.76, 131.03, 134.62, 175.11.

EXAMPLE 2

(3S)-2-Amino-2-Isobutyl-4-Pentenoic Acid a.
(3S,11R)-3-Isobutyl-5H,10bH-oxazolo[3,2-c][1,3]benzoxazine-2,5(3H)-dione Following the procedure described in example 1a with L-leucine afforded the title compound in 51% yield as fine needles mp=127°-128° C.; [α]$_D$=+108.40° (c=1,CH$_2$Cl$_2$); MS(DCI): 262(M+H)+ C$_{14}$H$_{15}$NO$_4$: Calculated C 64.36; H 5.79; N 5.36 : Found C 64.31; H 5.86; N 5.32

NMR(CDCl$_3$): 1.05 (d,3H,J=6 Hz), 1.10 (d,3H,J=6 Hz), 1.73-2.05 (m,3H), 4.76(d,½H,J=6 Hz), 4.79(d,½H,J=6 Hz), 6.62(s,1H), 7.16(d,1H,J=8 Hz), 7.29(dt,1H,J$_1$=8 Hz,J$_2$=1.5 Hz), 7.48(m,2H)

$^{13}$C NMR(CDCl$_3$): 21.56, 22.64, 24.86, 37.27, 56.79, 84.10, 112.97, 116.56, 125.10,126.96,132.09,146.98,148.24,171.10.

b. ((3S,11R)-3-Isobutyl-3-[1-(2-propenyl)]-5H,10bH-oxazolo-[3,2-c][1,3]benzoxazine-2,5(3H)-dione Following the procedure described in example 1b, the resultant compound from example 2a (1.85 g, 7.1 mmol) was treated with LiHMDS (6.9 ml, 6.9 mmol), allyl bromide (1.7 g, 14 mmol), and DMPU (1.8 g, 14 mmol) in THF to afford the crude product (>97% ds). Recrystallization from ethyl acetate/hexane afforded the title compound as fine needles (730 mg, 81%).

mp=124°-125° C.; [α]$_D$=96.92° (c=1.08, CH$_2$Cl$_2$); MS(DCI): 302(M+H)+,319(M+NH$_4$)+; C$_{17}$H$_{19}$NO$_4$: Calculated C 67.76; H 6.36; N 4.65: Found C 67.76; H 6.57; N 4.65. NMR(CDCl$_3$): 0.98(d,3H,J=4 Hz), 1.03(d,3H,J=4 Hz), 1.80(m,1H), 2.28(m,1H), 2.50(dd,1H, J$_1$=10 Hz,J$_2$=3 Hz), 3.13(dd,1H, J$_1$=10 Hz,J$_2$=5 Hz), 4.80(d,1H,J=8 Hz), 5.05(d,1H,J=10 Hz), 5.22(m,1H), 6.48(s,1H), 7.12(d,1H,J=5 Hz), 7.25(t,1H,J=5 Hz), 7.40(m,2H). $^{13}$C NMR(CDCl$_3$): 23.16, 24.11, 25.02, 39.17, 44.55, 66.47, 83.52, 116.45, 118.21, 121.46, 124.05, 125.21, 129.66, 131.07, 145.81, 148.38, 173.04.

c. (3S)-2-Amino-2-Isobutyl-4-Pentenoic Acid

Following the procedure described in example 1c, hydrolysis of the resultant compound from example 2b (226 mg, 0.76 mmol) with LiOH (1.3 g, 30 mmol) in aqueous dioxane (110 ml) afforded the title compound as a colorless powder (103 mg, 80%).

[α]$_D$=+61.43° (c=1,H$_2$O); MS(FAB): 172(M+H)+; NMR(CD$_3$OD): 0.95(d,3H,J=1.5 Hz),0.98(d,3H,J=1.5 Hz), 1.62-1.90(m,2H), 2.42(dd,1H,J$_1$=15 Hz,J$_2$=8 Hz), 2.63(dd,1H,J$_1$=15 Hz,J$_2$=6 Hz), 5.23(s,1H), 5.28(d,1H,J=6 Hz), 5.74(m,1H), $^{13}$C NMR(CD$_3$OD): 21.20, 22.93,23.15, 41.38, 43.77, 63.14, 120.73, 129.86, 175.09.

d. Alternative Preparation of (3S)-2-Amino-2-Isobutyl-4-Pentenoic Acid

The resultant compound from example 2b (230 mg, 0.76 mmol) was dissolved in 10 ml of 4N HCl/dioxane and 10 ml of water was added. The solution was refluxed for 1 h under a nitrogen atmosphere. The cooled solution was concentrated to about 2 ml and then diluted with 10 ml of water. This solution was extracted with CH$_2$Cl$_2$ and ether and then applied to 15 g of Dowex AG-X8 ion exchange resin. The column was eluted with water followed by 1.3N NH$_4$OH and ninhydrin positive fractions were pooled and concentrated to afford a tan solid. The solid was dissolved in water and filtered through a C-18 Sep-Pak cartridge, eluting first with water and then with 20% aqueous methanol. The eluent was concentrated and dried to afford a colorless solid (60 mg, 46%).

EXAMPLE 3

(2S)-2-Amino-2-Methyl-3-Phenylpropanoic Acid a. (3S, 11R)-3-Benzyl-3-Methyl-5H,10bH oxazolo[3,2c][1,3]benzoxazine-2,5(3H)-dione Following the procedure described in example 1b, the resultant compound from example 1a(886 mg,3 mmol) was treated with LiHMDS(2.94 ml, 2.94 mmol)-,methyl iodide(851 mg,6 mmol)and DMPU(770 mg,6 mmol)in THF to afford the crude product(78% ds). Column chromatography on neutral alumina afforded the title compound as a colorless solid (600 mg, 66%).

mp=137°-138° C.; [α]$_D$=+175.20° (c=1.02,CH$_2$Cl$_2$) ; MS(DCI): 310(M+H)+, 327(M+NH$_4$)+: C$_{18}$H$_{15}$NO$_4$: Calculated C 69.09; H 4.89; N 4.53 : Found C$_{70.01}$; H 4.97; N 4.49

NMR(CDCl$_3$): 1.84 (s,3H), 3.26(d,1H,J=14 Hz), 3.53(d,1H,J=14 Hz), 4.85(s,1H), 7.10-7.42(m,9H)

$^{13}$C NMR(CDCl$_3$) : 22.70, 41.56, 64.64, 83.32, 116.40, 118.02, 132.72, 124.93, 127.78, 128.99, 129.36, 130.81, 134.79, 145.57, 148.40, 173.13.

b. (2S)-2-Amino-2-Methyl-3-Phenylpropanoic Acid

Following the procedure described in example 1c, hydrolysis of the resultant compound from example 3a (190 mg, 0.614 mmol) with LiOH (1.03 g, 24.6 mmol) in aqueous dioxane (85 ml) afforded the title compound as a colorless powder (105 mg, 95%).

[α]$_D$=−19.1° (c=1.04,H$_2$O), Lit [α]$_D$=−20.7° (c=0.805,H$_2$O) for S isomer; MS(FAB): 180(M+H)+; NMR(D$_2$O) 1.57(s,3H), 3.01(d,1H,J=14 Hz), 3.31(d,1H,J=14 Hz), 7.26-7.45(m,5H). $^{13}$C NMR(D$_2$O): 22.92, 43.21, 62.69, 128.35, 129.501, 130.54, 134.77, 176.65.

EXAMPLE 4

(2S)-2-Amino-2-Benzylbutanoic Acid a. (3S,11R)-3-Benzyl-3-Ethyl-5H,10bH-oxazolo-[3,2-c][1,3]benzoxazine-2,5(3H)-dione Following the procedure described in example 1b,the resultant compound from example 1a(886 mg,3 mmol) was treated with LiHMDS (2.94 ml, 2.94 mmol), ethyl iodide (936 mg,6 mmol) and DMPU (770 mg, 6 mmol) in THF to afford the crude product (94%ds). Chromatography on neutral alumina afforded the title compound (445 mg, 69%).

mp=138°-141° C.; [α]$_D$=+169.7°; MS(DCI): 324(M+H)+, 341(M+NH$_4$)+; C$_{19}$H$_{17}$NO$_4$: Calculated C70.58; H 5.30; N 4.33 : Found C 70.27; H 5.32; N 4.30. NMR (CDCl$_3$): 0.64 (t,3H,J=7.5 Hz), 2.04(m,1H), 2.62(m,1H), 3.24(d,1H,J=14 Hz), 3.52(d,1H,J=14 Hz), 4.90(s,1H),7.10-7.42(m,9H). $^{13}$C NMR (CDCl$_3$): 8.29, 27.34, 41.47, 69.85, 83.44, 116.57, 118.04, 123.96, 125.26, 127.89, 129.15, 129.62, 130.99, 134.94, 145.87, 148.41, 172.90.

b. (2S)-2-Amino-2-Benzylbutanoic Acid

Following the procedure described in example 1c, hydrolysis of the resultant compound from example 4a (250 mg, 0.774 mmol) with LiOH (1.31 g, 31 mmol) in aqueous dioxane (110 ml) afforded the title compound as a colorless powder (140 mg, 94%).

[α]$_D$=−26.86° (c=2.1,H$_2$O), Lit [α]$_D$=−22.8° (c=2, H$_2$O) for S isomer ; MS(FAB): 194(M+H)+; NMR(D$_2$O): 0.97(t,3H,J=7 Hz), 1.82(m,1H), 2.06(m,1H), 3.01(d,1H,J=15 Hz), 3.32(d,1H,J=15 Hz), 7.25-7.45(m,5H). $^{13}$C NMR(D$_2$O): 7.92, 29.79, 42.18, 66.95, 128.39, 129.53, 130.60, 134.61, 175.58.

c. Alternative Preparation Of (2S)-2-Amino-2-Benzylbutanoic Acid

A mixture of the resultant compound from example 4a (200 mg, 0.6 mmol) and 3 g of SiO$_2$/FeCl$_3$ in 8 ml of 6N HCl was refluxed for three h. The cooled mixture was filtered and the solid was washed with 6N HCl and then with CH$_2$Cl$_2$. The aqueous layer was separated and washed with CH$_2$Cl$_2$ and ether and then concentrated to 5 ml and applied to 15 g of Dowex AG-X8 ion exchange resin. The column was eluted with water followed by 1.3N NH$_4$OH. The ninhydrin positive fractions were pooled and concentrated to afford a light pink solid. The solid was dissolved in water and then passed through a C-18 Sep-Pak filter. The product was eluted with water and 50% aqueous methanol. The eluent was concentrated and dried in vacuo to afford a light pink solid (104 mg, 90%).[α]$_D$= −27.24° (c=1, H$_2$O).

EXAMPLE 5

(2S)-2-Amino-2,4-Dimethylpentanoic Acid a. (3S,11R)-3-Isobutyl-3-Methyl-5H,10bH-oxazolo-[3,2-c]-[1,3]benzoxazine-2,5(3H)-dione Following the procedure described in example 1b, the resultant compound from example 2a (810 mg, 3.1 mmol) was treated with methyl iodide (850 mg, 6 mmol), LiHMDS (3 ml, 3 mmol) and DMPU (770 mg, 6 mmol) in THF to provide the crude product (66%ds). The crude product was passed through a short column of florisil and eluted with 10% ethyl acetate/hexane. The eluent was concentrated to afford a colorless solid (670 mg, 82%).

MS(DCI): 276(M+H)$^+$, 293(M+NH$_4$)$^+$: C$_{15}$H$_{17}$NO$_4$: Calculated C 65.44; H 6.22; N 5.09 : Found C 65.33; H 6.28; N 5.05. NMR of major isomer(CDCl$_3$): 1.01(d,3H,J=6 Hz), 1.04(d,3H,J=6 Hz), 1.70(s,3H), 1.80-2.0(m,2H), 2.18-2.28(m,1H), 6.50(s,1H), 7.18(m,1H), 7.28(m,1H), 7.47(m,2H). NMR of minor isomer: 0.69(d,3H,J=7 Hz), 0.89(d,3H,J=7 Hz), 1.67(s,3H), 6.46(s,1H).

b. (2S)-2-Amino-2,4-Dimethylpentanoic Acid

Following the procedure described in example 1c, hydrolysis of the resultant compound from example 5a (225 mg, 0.82 mmol) with LiOH (1.38 g, 33 mmol) in aqueous dioxane (110 ml) afforded the title compound as a colorless powder (103 mg, 87%).

[α]$_D$= +22.8° (c=3,H$_2$O), Lit [α]$_D$= +34.2° (c=3,H$_2$O) for S isomer. MS(DCI): 146(M+H)$^+$, 163(M+NH$_4$)$^+$; NMR (D$_2$O): 0.91(d,3H,J=6 Hz), 0.95(d,3H,J=6 Hz), 1.47(s,3H), 1.65-1.75 1.75(m,2H), 1.80-1.90(m,1H). $^{13}$C NMR(D$_2$O): 22.40, 24.20, 24.25, 24.68, 46.46, 61.55, 178.05.

EXAMPLE 6

(2R)-2-Amino-2-Methyl-4-Pentenoic Acid a. (3S, 11R)-3-Methyl-5H,10bH-oxazolo[3,2-c][1,3]benzoxazine-2,5(3H)-dione.

The procedure described in example 1 was modified in that the crude reaction mixture from L-alanine, salicylaldehyde and triphosgene was filtered and concentrated to afford a tan solid. This solid was continuously extracted with ethyl acetate and the organic solution was concentrated. The residue was recrystallized from ethyl acetate-hexane to afford the title compound as colorless needles in 45% yield. mp=165°-166° C.; [α]$_D$= +154.93° (c=1,CH$_2$Cl$_2$) MS(DCI): 220(M+H)$^+$ C$_{11}$H$_9$NO$_4$: Calculated C 60.28; H 4.14; N 6.39 : Found C 60.14 ; H 4.20 ; N 6.34 NMR (CDCl$_3$): 1.68 (d,3H, J=8.4 hz), 4.75 (q,1H, J=8.4 hz), 6.65 (s,1H),7.17 (d,1H, J=7.5 hz), 7.30 (dt,1H, J$_1$=7.5 hz,J$_2$=1.5 hz), 7.48 (m,2H) $^{13}$C NMR (CDCl$_3$): 14.30, 53.62, 83.71, 113.90, 116.85, 25.38, 126.56, 132.15, 146.50, 148.32, 171.20 b. (3R,11R)-3-Methyl-3-[1-(2-propenyl)-5H,10bH-oxazolo-[3,2-c][1,3]benzoxazine-2,5(3H)-dione Following the procedure described in example 1b, the resultant compound from example 6a (671 mg, 3 mmol) was treated with allyl bromide (520 mg, 6 mmol), LiHMDS (5.94 ml, 5.94 mmol) and DMPU (720 mg, 6 mmol) in THF to afford the crude product (83% d.s). Purification on silica gel afforded the title compound as a colorless solid (560 mg, 74%).

MS(DCI): 260(M+H)$^+$, 276(M+NH$_4$)$^+$; C$_{14}$H$_{13}$NO$_4$: Calculated C 64.86; H 5.05; N 5.40: Found C 64.77; H 5.02; N 5.29. NMR(CDCl$_3$) 1.70(s,1H), 2.52(m,1H), 3.27(dd,1H,J$_1$=15 Hz,J$_2$=8 Hz), 4.91(m,½H), 4.94(m,½H), 5.08(m,½H), 5.14(m,½H), 5.28-5.41(m,1H), 6.47(s,1H), 7.15(m,1H), 7.27(dd,1H,J$_1$=8 Hz,J$_2$=1.5 Hz), 7.43(m,1H).

c. (2R)-2-Amino-2-Methyl-4-Pentenoic Acid

Following the procedure described in example 1c, hydrolysis of the resultant compound from example 192 (259 mg, 1 mmol) with LiOH (2.1 g, 40 mmol) in aqueous dioxane (150 ml) afforded the crude product which was treated with Boc$_2$O (880 mg) and NaOH(40 mg) in aqueous dioxane (10 ml). After 3 days, the reaction was terminated and the N-Boc amino acid was isolated to afford a colorless oil (175 mg). This product was dissolved in ether and treated with excess HCl/dioxane. After 8 h, the reaction was concentrated to afford a light yellow oil. Trituration with ether provided the title compound as a colorless solid (106 mg, 64%). [α]$_D$= +14.0° (c=1.3,D$_2$O), Lit [α]$_D$= +14.2° for the R isomer. MS(DCI): 130(M+H)$^+$; NMR(D$_2$O): 1.57(s,3H), 2.56(dd,1H,J$_1$=15 Hz, J$_2$=8 Hz), 2.71(dd,1H,J$_1$=15 Hz,J$_2$=6 Hz), 5.28(d,1H,J=5 Hz), 5.32(s,1H), 5.7-5.85(m,1H). $^{13}$C NMR(D$_2$O): 21.84, 41.38, 60.24, 122.74, 129.95, 174.3.

EXAMPLE 7

(S)-2-Amino-2-(3'-thiabutyl)-4-pentenoic acid a. (3S,11R)-3-(3'-thiabutyl)-10bH-oxazolo [3,2-c][1,3]benzoxazine-2(3H),5-dione Following the procedure described in example 1a, the condensation of L-methionine, salicylaldehyde, and triphosgene affords the title compound.

b. (3S,11R)-3-[1-(2-propenyl)]-3-(3'-thiabutyl)-10bH-oxazolo [3,2-c][1,3]benzoxazine-2(3H)-5-dione Following the procedure described in example 1b, the resultant compound from example 7a is treated with lithium bis(trimethylsilyl)amide, DMPU, and allyl bromide. Standard workup, as described in example 1b, and purification affords the title compound.

c. (S)-Amino-2-(3'-thiabutyl)-4-pentenoic acid

Following the procedure described in example 1c, the resultant compound from example 7b is treated with lithium hydroxide in aqueous dioxane. Standard workup, as described in example 7b, affords the title compound.

EXAMPLE 8

(R)-2-Amino-6-[(benzyloxycarbonyl)amino]-2-[1-(2-propenyl)]hexanoic acid a. (3S,11R)-3-{4'-[(benzyloxycarbonyl)amino]butyl}-10bH-oxazolo[3,2-c][1,3]benzoxazine-2(3H), 5-dione Following the procedure described in example 1a, the condensation of L-N$^6$-CBZ-lysine, salicylaldehyde, and triphosgene affords the title compound.

b. (3R,11R)-3-{4'-[(benzyloxycarbonyl)amino]butyl}-3-[1-(2-propenyl)]-10bH-oxazolo[3,2-c][1,3]benzoxazine-2(3H), 5-dione Following the procedure described in example 1b, the resultant compound from example 8a is treated with lithium bis(trimethylsilyl)amide (two equivalents), DMPU, and allyl bromide. Standard workup and purification affords the title compound.

c. (R)-2-Amino-6-[(benzyloxycarbonyl)amino]-2-[1-(2-propenyl)]hexanoic acid Following the procedure described in example 1c, the resultant compound from example 8b is treated with lithium hydroxide in aqueous dioxane. Standard workup and purification affords the title compound.

EXAMPLE 9

(R)-2 Amino-2-fluoro-3-phenylpropanoic acid (3R,11R)-3-Fluoro-3-Phenylmethyl-10bH-Oxazolo[3,2-c][1,3] benzoxazine-2(3H), 5-dione Following the procedure described in example 1b, the resultant compound from example 1a is treated with lithium bis(trimethylsilyl)amide, DMPU, and N-fluoro-3,3-dimethyl-2,3-dihydro-1,2-benzthiazol-1,1-dioxide (prepared according to Differding and Lang, Helv. Chim. Acta.,1989,72, 1248–1252). Standard workup and purification affords the title compound.

b. (R)-2 Amino-2-fluoro-3-phenylpropanoic acid

Following the procedure described in example 1c, the resultant compound from example 9a is treated with lithium hydroxide in aqueous dioxane. Standard workup and purification affords the title compound.

EXAMPLE 10

(R)-2-Amino-2-[1-(2-propenyl)]1glutaric Acid a. (3S,11R)-3-(2-carbomethoxyethyl)-10bH-oxazolo[3,2-c][1,3] benzoxazine-2(3H), 5-dione Following the procedure described in example 1a, the condensation of L-glutamic acid δ-methyl ester with salicylaldehyde and triphosgene affords the title compound.

b. (3S,11R)-3-(2-carbomethoxyethyl)-3-[1-(2-propenyl)]-10bH-oxazolo[3,2-c][1,3] benzoxazine-2(3H), 5-dione Following the procedure described in example 1b, the resultant compound from example 10a is treated with lithium bis(trimethylsilyl)amide, DMPU, and allyl bromide. Standard workup and purification affords the title compound.

c. (R)-2-Amino-2-[1-(2-propenyl)]glutaric Acid

Following the procedure described in example 1c, the resultant compound from example 10b is treated with lithium hydroxide in aqueous dioxane. Standard workup and purification affords the title compound.

EXAMPLE 11

Methyl (S)-2-[(Methoxycarbonyl)amino]-2-Phenylmethyl-4-Pentenoic Acid

A solution of the resultant compound from example 1b (336 mg, 1 mmol) in dry methanol(10 ml) was added to a solution of sodium methoxide( prepared by dissolving 920 mg of sodium metal in 140 ml of dry methanol). The yellow solution was stirred at room temperature for 20 min and then neutralized wih 12N HCl. The mixture was concentrated and the residue was partitioned between ethyl acetate(200 ml) and water(100 ml). The layers were separated and the organic layer was washed with saturated aqueous sodium bicarbonate, brine, and dried over sodium sulfate. The filtered solution was concentrated in vacuo and the residue was dissolved in diethyl ether and passed through a 6" column of basic alumina. The column was eluted with ether(200 ml) and the eluent was concentrated to afford the title compound as a light yellow oil(218 mg, 79%). $[\alpha]_D = 49.66°$ (c=1, $CH_2Cl_2$); MS (DCI):278(M+H)$^+$, 295(M+NH$_4$)$^+$.

EXAMPLE 12

Benzyl-(S)-2-[(Benzyloxycarbonyl)amino]-2-Phenylmethyl-4-Pentenoic Acid

A solution of the resultant compound from example 1b (336 mg, 1 mmol) in dry THF(10 ml) was added to a solution of sodium benzyloxide (prepared by adding 1.6 g of sodium hydride to 120 ml of dry benzyl alcohol). The yellow solution was stirred at room temperature for 20 min. and then concentrated in vacuo. The residue was partitioned between ethyl acetate and saturated aqueous ammonium chloride. The layers were separated and the organic layer was dried over sodium sulfate and concentrated to afford a golden oil. Chromatography on silica gel using ethyl acetate/hexane mixtures afforded the title compound as a light yellow oil (345 mg, 80%). $[\alpha]_D = +12.16°$ (c=1, $CH_2Cl_2$); MS (DCI):430(M+H)$^+$.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. The substantially pure compound of the formula:

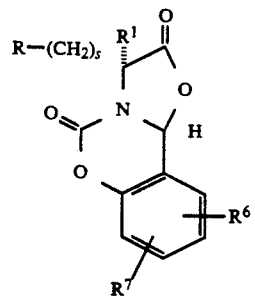

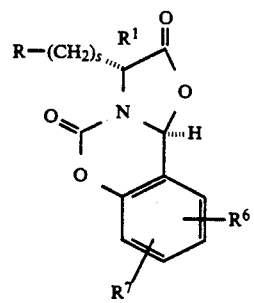

wherein s is 0 to 4; R is (i) loweralkyl, (ii) cycloalkyl, (iii) loweralkenyl, (iv) loweralkynyl, (v) aryl wherein aryl is selected from phenyl, naphthyl, tetrahydronaphthyl, indanyl and biphenyl with the aryl group being unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide, (vi) arylalkyl wherein aryl is defined as above, (vii) heterocyclic wherein the heterocyclic is selected from pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl with the heterocyclic being unsubstituted or substituted with one or two substituents independently selected from hydroxy, halo, oxo (=O), amino, alkylamino, dialkylamino, alkoxy, polyalkoxy, haloalkyl, cycloalkyl, aryl, arylalkyl, carboxy, —SO$_3$H and loweralkyl, (viii) (heterocyclic)alkyl wherein heterocyclic is defined as above, (ix) —COOH, (x) alkoxycarbonyl, (xi) —(CH$_2$)$_m$—Q—R$^3$ wherein m is 0 to 4, Q is O or S and R$^3$ is hydrogen, loweralkyl, an O-protecting group or an S-protecting group, or (xii) —(CH$_2$)$_p$—N(R$^4$)(R$^5$) wherein p is 0 to 4 and R$^4$ and R$^5$ are independently selected from hydrogen, loweralkyl and an N-protecting group; R$^1$ is loweralkyl, —(CH$_2$)$_u$CN wherein u is 1 to 3, cycloalkylalkyl, halo, loweralkenyl, loweralkynyl, arylalkyl wherein aryl is defined as above, (heterocyclic)alkyl wherein heterocyclic is defined as above or —(CH$_2$)$_z$CH(OR″)(OR‴) wherein z is 1 to 3 and R″ and R‴ are loweralkyl or aryl wherein aryl is defined as above or R″ and R‴ taken together are —(CH(R$^0$))$_t$— wherein t is 2 to 3 and R$^0$ is independently selected at each occurrence from hydrogen, loweralkyl and aryl wherein aryl is defined as above; and R$^6$ and R$^7$ are independently selected from hydrogen, loweralkyl, halogen, nitro, alkoxy, haloalkyl and alkoxycarbonyl.

2. The compound of claim 1 wherein R is loweralkyl, benzyl, alkoxycarbonylethyl, 3'-thiabutyl or 4'-(benzyloxycarbonyl)amino)butyl and R$^1$ is unsubstituted loweralkenyl, loweralkyl, unsubstituted loweralkynyl or halo.

3. The substantially pure compound of the formula:

wherein s is 0 to 4; R is (i) loweralkyl, (ii) cycloalkyl, (iii) loweralkenyl, (iv) loweralkynyl, (v) aryl wherein aryl is selected from phenyl, naphthyl, tetrahydronaphthyl, indanyl and biphenyl with the aryl group being unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide, (vi) arylalkyl wherein aryl is defined as above, (vii) heterocyclic wherein the heterocyclic is selected from pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl with the heterocyclic being unsubstituted or substituted with one or two substituents independently selected from hydroxy, halo, oxo (=O), amino, alkylamino, dialkylamino, alkoxy, polyalkoxy, haloalkyl, cycloalkyl, aryl, arylalkyl, carboxy, —SO$_3$H and loweralkyl, (viii) (heterocyclic)alkyl wherein heterocyclic is defined as above, (ix) —COOH, (x) alkoxycarbonyl, (xi) —(CH$_2$)$_m$—Q—R$^3$ wherein m is 0 to 4, Q is O or S and R$^3$ is hydrogen, loweralkyl, an O-protecting group or an S-protecting group, or (xii) —(CH$_2$)$_p$—N(R$^4$)(R$^5$) wherein p is 0 to 4 and R$^4$ and R$^5$ are independently selected from hydrogen, loweralkyl and an N-protecting group; R$^1$ is loweralkyl, —(CH$_2$)$_u$CN wherein u is 1 to 3, cycloalkylalkyl, halo, loweralkenyl, loweralkynyl, arylalkyl wherein aryl is defined as above, (heterocyclic)alkyl wherein heterocyclic is defined as above or —(CH$_2$)$_z$CH(OR″)(OR‴) wherein z is 1 to 3 and R″ and R‴ are loweralkyl or aryl wherein aryl is defined as above or R″ and R‴ taken together are —(CH(R$^0$))$_t$— wherein t is 2 to 3 and R$^0$ is independently selected at each occurrence from hydrogen, loweralkyl and aryl wherein aryl is defined as above; and R$^6$ and R$^7$ are independently selected from hydrogen, loweralkyl, halogen, nitro, alkoxy, haloalkyl and alkoxycarbonyl.

4. The compound of claim 1 wherein R is loweralkyl, benzyl, alkoxycarbonylethyl, 3'-thiabutyl or 4'-((benzyloxycarbonyl)amino)butyl and R$^1$ is unsubstituted loweralkenyl, loweralkyl, unsubstituted loweralkynyl or halo.

5. A compound selected from the group consisting of:
(3S,11R)-3-Phenylmethyl-3-(1-(2-propenyl)-10bH-oxazolo-[3,2-c][1,3]benzoxazine-2(3H), 5-dione;
((3S,11R)-3-Isobutyl-3-[1-(2-propenyl)]-5H,10bH-oxazolo-[3,2-c][1,3]benzoxazine-2,5(3H)-dione;

(3S,11R)-3-Benzyl-3-Methyl-5H,10bH-oxazolo-[3,2c][1,3]benzoxazine-2,5(3H)-dione;
(3S,11R)-3-Benzyl-3-Ethyl-5H,10bH-oxazolo-[3,2-c][1,3]benzoxazine-2,5(3H)-dione;
(3S,11R)-3-Isobutyl-3-Methyl-5H,10bH-oxazolo-[3,2-c]-[1,3]benzoxazine-2,5(3H)-dione;
((3S,11R)-3-Methyl-3-[1-(2-propenyl)]-5H,10bH-oxazolo-[3,2-c][1,3]benzoxazine-2,5(3H)-dione;
(3S,11R)-3-[1-(2-propenyl)]-3-(3'-thiabutyl)-10bH-oxazolo [3,2-c][1,3]benzoxazine-2(3H)-5-dione;
(3R,11R)-3-{4'-[(benzyloxycarbonyl)amino]butyl)-3-[1-(2-propenyl)]-10bH-oxazolo[3,2-c][1,3]benzoxazine-2(3H),5-dione;
((3R,11R)-3-Fluoro-3-Phenylmethyl-10bH-Oxazolo[3,2-c][1,3]benzoxazine-2(3H),5-dione; and
(3S,11R)-3-(2-carbomethoxyethyl)-3-[1-(2-propenyl)]-10bH-oxazolo[3,2-c][1,3] benzoxazine-2(3H),5-dione.

* * * * *

UNITED STATES PATENT AND TRADEMARK OFFICE
CERTIFICATE OF CORRECTION

PATENT NO.: 5,268,476
DATED: December 7, 1993
INVENTOR(S): Thomas M. Zydowsky It is certified that error appears in the above-indentified patent and that said Letters Patent is hereby corrected as shown below:

COLUMN 13 LINE 34:   Delete "benzothlazolyl" and insert --benzothiazolyl--

COLUMN 14, LINE 32:   Delete "benzothlazolyl" and insert --benzothiazolyl--

COLUMN 15, LINE 7:   Delete "((3S,11R)" and insert --(3R,11R)--

COLUMN 16, LINE 6:   Delete "((3R,11R)" and insert --(3R,11R)--

Signed and Sealed this

Fifth Day of July, 1994

Attest:

BRUCE LEHMAN

*Attesting Officer*        *Commissioner of Patents and Trademarks*